United States Patent [19]

Bollé

[11] Patent Number: 4,689,837
[45] Date of Patent: Sep. 1, 1987

[54] EYE SHIELD WITH FACE ENGAGING SEAL

[75] Inventor: Robert Bollé, Oyonnax, France

[73] Assignee: Etablissements Bolle Georges, Robert et Maurice, Oyonnax, France

[21] Appl. No.: 736,326

[22] Filed: May 21, 1985

[30] Foreign Application Priority Data

May 21, 1985 [FR] France ............... 84 07851

[51] Int. Cl.[4] .............................................. A61F 9/02
[52] U.S. Cl. ......................................... 2/440; 2/428
[58] Field of Search ............... 2/428, 440, 441, 429, 2/430, 431, 435, 436, 437, 438, 15, 426; 128/206.24, 206.23; D16/101, 102, 108

[56] References Cited

U.S. PATENT DOCUMENTS

| 2,406,608 | 8/1946 | Joyce | 2/440 |
| 2,406,998 | 9/1946 | DuBois | 2/441 |
| 2,648,843 | 8/1953 | Hirschmann | 2/431 |
| 2,918,676 | 12/1959 | Matheson | 2/440 |
| 2,936,458 | 5/1960 | Luisada | 2/435 |
| 4,069,516 | 1/1978 | Watkins, Jr. | 2/428 |
| 4,353,134 | 10/1982 | MacNabb | 2/428 |

FOREIGN PATENT DOCUMENTS

| 1193639 | 5/1965 | Fed. Rep. of Germany . |
| 773077 | 11/1934 | France . |
| 906927 | 2/1946 | France . |
| 2302718 | 5/1976 | France | 2/426 |

Primary Examiner—Werner H. Schroeder
Assistant Examiner—Andrew M. Falik
Attorney, Agent, or Firm—Fleit, Jacobson, Cohn & Price

[57] ABSTRACT

A mask to be worn flush on the face, consists of a case delimited by a frame, and open on one side to the face. The frame includes a flange consisting of two rims extending in both directions of the plane of the frame and transverse to the frame. The frange is extended by a flexible cushion which extends towards the wearer's face, on both sides of the frame and which is curved inwardly, remote from the rim on which the cushion is cantilevered.

7 Claims, 2 Drawing Figures

EYE SHIELD WITH FACE ENGAGING SEAL

BACKGROUND OF THE INVENTION

The invention relates to a face-contacting mask, used as protective glasses or breathing apparatus, which is to be worn flush on the face. The invention relates more precisely to the points of contact on the wearer's face.

One prior-art device which resembles the device of the present invention, consists of a flexible foam frame which has certain disadvantages. This foam frame must be attached to the edge of the mask; this frame becomes soiled; its flexibility is limited and does not allow for a perfect fit for the various shapes of different faces.

Another prior-art device which resembles the device of the present invention consists of a flexible cushion made of plastic or elastomer which follows the edge of the mask, is attached to it, or is of one piece with it. Other masks exist which are fitted with a flexible cushion, the wearer's face bearing on this flexible cushion which may bend in the direction of the edge of the mask. The amount of flexion is however limited for the flexible cushion comes to rest against the edge of the mask, which is hard. The cushion's adaptability and the user's comfort are therefore restricted. Moreover a characteristic feature of the cushion is that it is fixed to one side of the edge of the mask i.e. either on the interior or exterior of the mask.

The efficiency in absorbing pressure does no relate evenly to pressure exerted on the interior or exterior edge of the mask.

Moreover certain masks are fitted with mobile contact flaps which bend to a considerable extent towards the interior of of the mask, wherein the absorption of the pressure is on one side of the edge of the mask only, viz. towards the inside. Finally, when these mobile contact flaps are flexed to a great extent, the eye piece of the mask comes into contact with the wearer.

SUMMARY OF THE INVENTION

One of the aims of the invention is to design a mask with face contact which reacts to an equal degree or pressure whether it comes from the outside or inside of the edge of the mask.

Another aim of the invention is the design of a mask with means of contact which may be bent gradually and to a great extent whilst keeping the eyepiece remote from the wearer's face.

This invention thus relates to a mask intended to be placed against the face and comprises a case delimited by a frame and open on the face side. This invention is characterised by the frame having a brim consisting of a flange extending in both directions of the plane of the said frame, and characterised by not being parallel with the frame. The brim is extended with a flexible cushion in the direction of the wearer's face, bot inside and outside this frame. It is inwardly curved, remote from the brim on which this cushion is cantilevered.

The flange is preferably perpendicular to the frame. The flexible cushion bears on the unengaged extremity of one of the two rims which form the flange.

Preferably, the flange and the cushion are symmetrically located with regard to the plane of the frame.

BRIEF DESCRIPTION OF THE DRAWINGS

By way of example only, specific embodiments and advantages of the invention will now be described with reference to the accompanying drawings in which.

DESCRIPTION OF THE PREFERRED EMBODIMENTS

Figure 1:
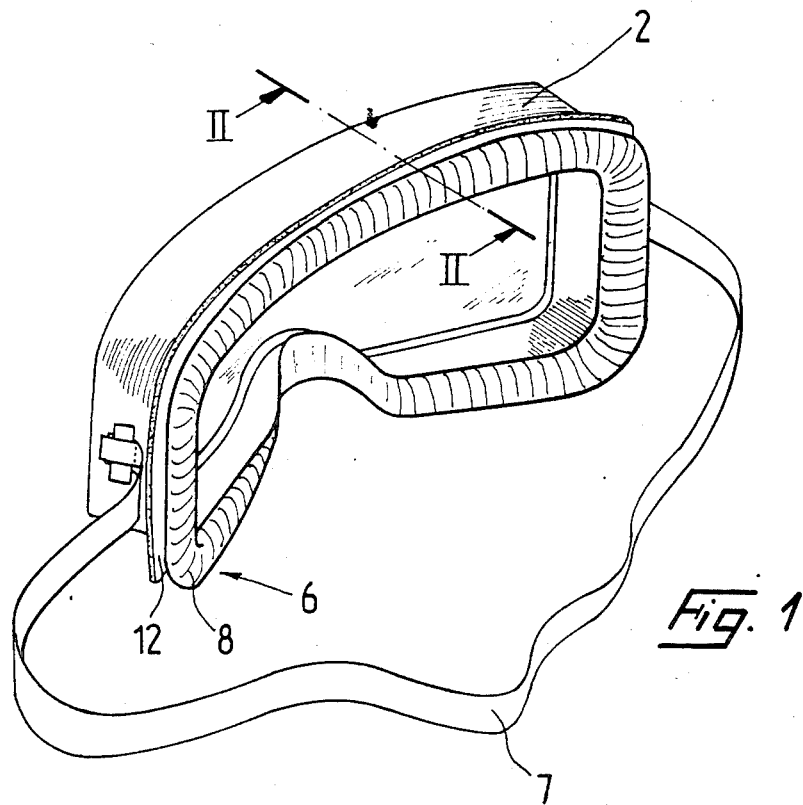
FIG. 1 is a perspective view of a mask of the eye protector type which is an embodiment of the invention.
Figure 2:
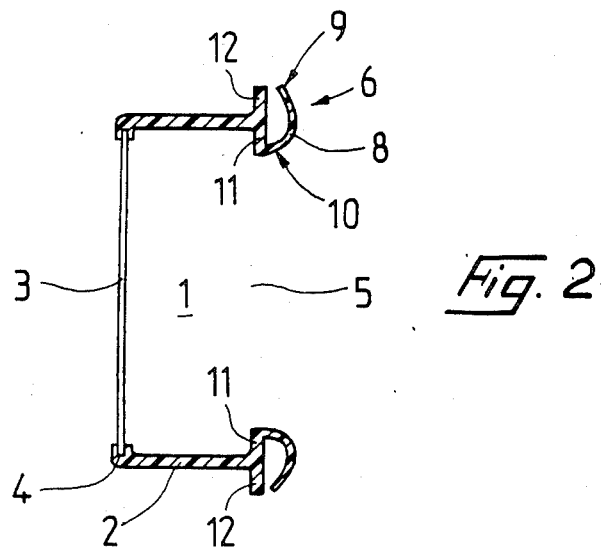
FIG. 2 is a cross section taken along line II—II of FIG. 1.

The mask illustrated in FIGS. 1 and 2 is intended to be worn in front of the eyes to protect the latter from external agents. It comprises a case, a prior-art device delimited by a continuous lateral frame (2) and by a visor (3) made of a transparent material, the periphery of which is attached to one of the edges of the frame (2) and fits in a groove (4) on the edge of the frame.

The case (1) thus has therefore an opening (5) remote from the visor (3). This opening Z5) is bordered with a flexible cushion (6) by which the mask bears on the face on which it is placed by means, in this embodiment, of an elastic strap (7).

The lateral frame (2) has, on the open side (5) a peripheral T section brim comprising an internal rim (11) extending towards the inside of the case (1) and an external rim (12) extending towards the outside of the case (1). These rims (11 & 12) are therefore perpendicular to the plane of the lateral frame (2). These rims (11 and 12) may however extend obliquely to the lateral frame (2), but cannot be parallel to this frame (2).

A flexible cushion (8) is affixed to face the rims (11 and 12) and is curved, away from these rims (11 and 12). The internal edge (10) of this flexible cushion (8) is attached to the unengaged edge of the interior rim (11) and the other edge (9) of the flexible cushion lies opposite to, but remote from, the unengaged edge of the exterior rim (12)

The case (1) of the mask consists of a prior-art device in thermoplastic material or elastomer shaped in one piece; the thermoplastic visor (3) is independent and fixed to the lateral frame (2). The necessary rigidity of the case (1) is achieved by using a visor (3) and a frame (2) of sufficient thickness. The flexibility of the rims (11 and 12) and of the cushion (8) is achieved by using a thinner section.

In practice, when the mask rests on the wearer's face the cushion (8) and the rims (11 and 12) of the edge of the frame (2) change their shape in two stages.

At the first stage, only the cushion (8) bends towards the rim (11 and 12). At the second stage, when subjected to greater pressure, the cushion (8) rests on one of the other rims (11 and 12) which themselves bend towards the frame (2). For example, in the case of pressure exerted in the direction of the exterior edge (9) of the cushion (8), the latter comes into contact with the rim (12) which now bends. Alternatively in case of pressure exerted in the direction of the interior edge (10) of the cushion (8), the latter comes into contact with the rim (11) which bends. As for the frame (2) of the mask, its rigidity is sufficient for it to hardly bend at all. It may even be designed so as not to bend at all.

It will be noted that the flexible points of the mask of the invention act symetrically and progressively according to internal and external pressure exerted on the mask. A great degree of flexibility and therefore of absorption is achieved; unlike existing masks, the flexible cushion (8), once it has changed its shape, does not lie against a rigid edge. Finally, the edges (11 and 12) are always kept at a distance from the visor (3) of the mask, as the frame (2) is sufficiently rigid and is perpendicular to the wearer's face.

Variations can be bought to the embodiment described above: in particular, the cushion (8) may be linked to the frame (2) by fixing its exterior edge to the unengaged extremity of the exterior rim (12); the cushion being now open towards the inside of the case (1).

We claim:

1. A mask to be placed flush against a wearer's face, said mask comprising:

a visor and a lateral frame which define an interior space, said lateral frame extends between said visor and the wearer's face essentially perpendicular to the wearer's face to space away the wearer's face from said visor a distance substantially equal to a length of said lateral frame, said lateral frame including flexible bearing means by which said mask bears on the wearer's face, said flexible bearing means comprises two flexible rims respectively extending from said lateral frame in a symmetrical arrangement towards the interior space and away from the interior space, said two flexible rims extending in a direction transverse to said lateral frame, a cushion mounted on one of said flexible rims, extending in a cantilever manner from said one flexible rim towards the other flexible rim, and being curved towards said other flexible rim, so that when said visor is impacted, said cushion will in a first position deform to absorb the impact and under sufficient force will in a second position transmit pressure to at least one of said two flexible rims, which will also deform to absorb such pressure, thereby providing a two position deformation while spacing said lateral frame and said visor from the wearer's face to avoid impacting the wearer's face with said visor.

2. A mask according to claim 1, wherein said lateral frame is substantially less flexible that said flexible bearing means.

3. A mask according to claim 2, wherein said lateral frame and said bearing means are made of one piece, said lateral frame having a thicker cross section that said bearing means.

4. A mask according to claim 1, wherein said two flexible rims extend perpendicular to said lateral frame.

5. A mask for protecting the face of a wearer, said mask comprising:

a frame extending substantially perpendicular to the wearer's face, a visor mounted in one end of said frame, said visor being spaced away from the wearer's face by a distance subtantially equal to a length of said frame, and flexible bearing means mounted at the other end of said frame for adjusting said mask on the face of a wearer, said flexible bearing means including two flexible rims, each flexible rim being mounted at one end or the other end of said frame and extending transverse to said frame in a symmetrical arrangement, the other end of one of said two flexible rims includes a flexible cushion mounted thereon at one end of said one flexible rim, said flexible cushion curves from said one flexible rim towards said other flexible rim and terminates adjacent the other end of said other flexible rim so that when said visor is impacted, said flexible cushion will in a first position deform to absorb the impact and under sufficient force will in a second position transmit pressure to at least one of said two flexible rims, which will also deform to absorb such pressure, thereby providing a two position deformation while spacing said frame and said visor from the wearer's face to avoid impacting the wearer's face with said visor.

6. A mask according to claim 5, wherein said two flexible rims extend perpendicular to said frame.

7. A mask according to claim 5, wherein said frame is less flexible than said flexible bearing means.

* * * * *